(12) United States Patent
Vance et al.

(10) Patent No.: US 7,727,717 B2
(45) Date of Patent: Jun. 1, 2010

(54) METHODS OF DETECTING CHARCOT-MARIE TOOTH DISEASE TYPE 2A

(75) Inventors: Jeffery M Vance, Chapel Hill, NC (US);
Stephan Zuchner, Durham, NC (US);
Margaret A. Pericak-Vance, Chapel Hill, NC (US)

(73) Assignee: Duke University, Durham, NC (US)

( * ) Notice: Subject to any disclaimer, the term of this patent is extended or adjusted under 35 U.S.C. 154(b) by 816 days.

(21) Appl. No.: 10/987,174

(22) Filed: Nov. 12, 2004

(65) Prior Publication Data

US 2005/0181390 A1 Aug. 18, 2005

Related U.S. Application Data

(60) Provisional application No. 60/520,429, filed on Nov. 14, 2003.

(51) Int. Cl.
*C12Q 1/70* (2006.01)
*C12P 19/34* (2006.01)

(52) U.S. Cl. .......................................... 435/6; 435/91.1

(58) Field of Classification Search ........................ None
See application file for complete search history.

(56) References Cited

U.S. PATENT DOCUMENTS

| 6,127,159 | A | 10/2000 | Fuller et al. | |
|---|---|---|---|---|
| 6,150,160 | A * | 11/2000 | Kazazian et al. | 435/320.1 |
| 6,284,507 | B1 | 9/2001 | Fuller et al. | |
| 6,316,213 | B1 * | 11/2001 | O'Brien | 435/23 |
| 2002/0168673 | A1 | 11/2002 | Fuller et al. | |

FOREIGN PATENT DOCUMENTS

WO WO 01/25274 A1 4/2001

OTHER PUBLICATIONS

Landegren et al; Genome Research, vol. 8, 1998, pp. 769-776.*
dbSNP rs1042836, pp. 1-3; NCBI.*
Genbank Accession No. NM_014874.*
Engelfried et al; BMC Medical Genetics, 2006, 7:53, pp. 1-7.*
Pennisi, Science, 1998; 281 (5384):1787-1789.*
Hacker et al; Gut, 1997, vol. 40, pp. 623-627.*
Santel at al; Journal of Cell Science, vol. 114, pp. 867-874.*
Gemignani et al; Journal of Neurological Sciences, vol. 184, pp. 1-9, 2001.*
Database GenBank XP002329547, Database Accession No. NM_014874, printed Nov. 17, 2005.*
dbSNP rs1042836, pp. 1-3 NCBI, printed Jul. 19, 2007.*
Santel et al. Journal of Cell Science, vol. 114, pp. 867-874, 2001.*
Chen, H., et al., "Mitofusins Mfnl and Mfn2 Coordinately Regulate Mitochondrial Fusion and are Essential for Embryonic Development," *The Journal of Cell Biology*, 160(2): 189-200 (2003).
Database Genbank XP002329547, Database Accession No. NM_014874.
Gemignani, F., et al., "Charcot-Marie-Tooth Disease (CMT): Distinctive Phenotypic and Genotypic Features in CMT Type 2," *Journal of Neurological Sciences*, 184(1): 1-9 (2001).
Ben Asher, E. and Lancet, D., "A New Gene for the Charcot-Marie-Tooth Disorder," *Ir. Med. Assoc. J.*, 6: 376-377 (2004).
Bissar-Tadmouri, N., et al., "Absence of KIF1B Mutation in a Large Turkish CMT2A Family Suggests Involvement of a Second Gene," *Neurology*, 62: 1522-1525 (2004).
Bradbury, J., "Mitochondrial Fusion Protein Mutated in CMT2A," *Lancet Neurol.*, 3: 326 (2004).
Hales, K.G., et al., "Developmentally Regulated Mitochondrial Fusion Mediated by a Conserved, Novel, Predicted GTPase," *Cell*, 90: 121-129 (1997).
Hermann, G.J., et al., "Mitochondrial Fusion in Yeast Requires the Transmembrane GTPase Fzolp," *Journal of Cell Biology*, 143:359-373 (1998).
Kijima, K., et al., "Mitochondrial GTPase Mitofusion 2 Mutation in Charcot-Marie-Tooth Neuropathy Type 2A," *Human Genetics*, 116: 23-27 (2005).
Muglia, M., et al., "Clinical and Generic Study of a Large Charcot-Marie-Tooth Type 2A Family From Southern Italy," *Neurology*, 56: 100-103 (2001).
Santel, A. and Fuller, M.T., "Control of Mitochondrial Morphology by a Human Mitofusion," *Journal of Cell Science*, 114: 867-874 (2000).
Zhao, C., et al. "Charcot-Marie-Tooth Disease Type 2A Caused by Mutation in a Microtubule Motor KIF-1Bβ," *Cell*, 105: 587-597 (2001).
Zuchner, S., et al., "Mutations in the Mitochondrial GTPase Mitofusion 2 Cause Charcot-Marie-Tooth Neuropathy," *Nature Genetics*, 36: 449-451 (2004).

* cited by examiner

*Primary Examiner*—Sarae Bausch
(74) *Attorney, Agent, or Firm*—Hamilton, Brook, Smith & Reynolds, P.C.

(57) ABSTRACT

Methods are described for screening a subject for risk of Charcot-Marie-Tooth Disease Type 2A or for diagnosing Charcot-Marie-Tooth disease or a predisposition for developing Charcot-Marie-Tooth disease in a subject, by detecting the presence or absence of a mutation in the mitofusin gene in a biological sample collected from the subject. Methods are also described for detecting the presence of a genetic polymorphism associated with Charcot-Marie-Tooth Disease Type 2A in a sample of patient nucleic acid, by amplifying a mitofusin gene sequence in the patient nucleic acid to produce an amplification product; and identifying the presence of a Charcot-Marie-Tooth Disease Type 2A associated polymorphism in the amplification product.

20 Claims, 5 Drawing Sheets

```
                           SEQUENCE LISTING

<160> NUMBER OF SEQ ID NOS: 65

<210> SEQ ID NO 1
<211> LENGTH: 52
<212> TYPE: PRT
<213> ORGANISM: Homo sapiens

<400> SEQUENCE: 1

Pro Val Thr Thr Glu Glu Gln Val Leu Asp Val Lys Gly Tyr Leu Ser
 1               5                  10                  15

Lys Val Arg Gly Ile Ser Glu Val Leu Ala Arg Arg His Met Lys Val
            20                  25                  30

Ala Phe Phe Gly Arg Thr Ser Asn Gly Lys Ser Thr Val Ile Asn Ala
        35                  40                  45

Met Leu Trp Asp
    50

<210> SEQ ID NO 2
<211> LENGTH: 52
<212> TYPE: PRT
<213> ORGANISM: M. musculus

<400> SEQUENCE: 2

Pro Val Thr Thr Glu Glu Gln Val Leu Asp Val Lys Gly Tyr Leu Ser
 1               5                  10                  15

Lys Val Arg Gly Ile Ser Glu Val Leu Ala Arg Arg His Met Lys Val
            20                  25                  30

Ala Phe Phe Gly Arg Thr Ser Asn Gly Lys Ser Thr Val Ile Asn Ala
        35                  40                  45

Met Leu Trp Asp
    50

<210> SEQ ID NO 3
<211> LENGTH: 50
<212> TYPE: PRT
<213> ORGANISM: D. melanogaster

<400> SEQUENCE: 3

Val Asp Lys Ala Glu Arg Glu Leu Phe Glu Ser Tyr Val Tyr Lys Val
 1               5                  10                  15

Ala Ala Ile Arg Glu Val Leu Gln Arg Asp His Met Lys Val Ala Phe
            20                  25                  30

Phe Gly Arg Thr Ser Asn Gly Lys Ser Ser Val Ile Asn Ala Met Leu
        35                  40                  45

Arg Glu
    50

<210> SEQ ID NO 4
<211> LENGTH: 51
<212> TYPE: PRT
<213> ORGANISM: C. elegans
```

```
<400> SEQUENCE: 4

Phe Val Ser Ser Glu Gln Arg Glu Ile Glu Ala Ile Gly Asp Ser
 1               5                  10                  15

Ile Lys Thr Ile Met Asp Thr Phe Gln Arg Asp Asn Met Lys Val Val
             20                  25                  30

Phe Phe Gly Arg Thr Ser Asn Gly Lys Ser Thr Thr Ile Asn Ala Met
         35                  40                  45

Leu His Glu
     50

<210> SEQ ID NO 5
<211> LENGTH: 52
<212> TYPE: PRT
<213> ORGANISM: Homo sapiens

<400> SEQUENCE: 5

Arg Ile Ala Thr Glu Asp Asp Leu Val Glu Met Gln Gly Tyr Lys Asp
 1               5                  10                  15

Lys Leu Ser Ile Ile Gly Glu Val Leu Ser Arg Arg Asx Met Lys Val
             20                  25                  30

Ala Phe Phe Gly Arg Thr Ser Ser Gly Lys Ser Ser Val Ile Asn Ala
         35                  40                  45

Met Leu Trp Asp
     50

<210> SEQ ID NO 6
<211> LENGTH: 52
<212> TYPE: PRT
<213> ORGANISM: M. musculus

<400> SEQUENCE: 6

Arg Ile Ala Ser Glu Asp Asp Leu Val Glu Ile Gln Gly Tyr Arg Asn
 1               5                  10                  15

Lys Leu Ala Val Ile Gly Glu Val Leu Ser Arg Arg Asx Met Lys Val
             20                  25                  30

Ala Phe Phe Gly Arg Thr Ser Ser Gly Lys Ser Ser Val Ile Asn Ala
         35                  40                  45

Met Leu Trp Asp
     50

<210> SEQ ID NO 7
<211> LENGTH: 37
<212> TYPE: PRT
<213> ORGANISM: Homo sapiens

<400> SEQUENCE: 7

Ser Leu Ser Arg Pro Asn Ile Phe Ile Leu Asn Asn Arg Trp Asp Ala
 1               5                  10                  15

Ser Ala Ser Glu Pro Glu Tyr Met Glu Glu Val Arg Arg Gln His Met
             20                  25                  30

Glu Arg Cys Thr Ser
         35

<210> SEQ ID NO 8
<211> LENGTH: 37
<212> TYPE: PRT
<213> ORGANISM: M. musculus

<400> SEQUENCE: 8
```

```
Ser Leu Ser Arg Pro Asn Ile Phe Ile Leu Asn Asn Arg Trp Asp Ala
1               5                   10                  15

Ser Ala Ser Glu Pro Glu Tyr Met Glu Glu Val Arg Arg Gln His Met
            20                  25                  30

Glu Arg Cys Thr Ser
        35

<210> SEQ ID NO 9
<211> LENGTH: 39
<212> TYPE: PRT
<213> ORGANISM: D. melanogaster

<400> SEQUENCE: 9

Ser Gln Lys Leu Ser Lys Pro Asn Ile Phe Ile Leu Asn Asn Arg Trp
1               5                   10                  15

Asp Ala Ser Ala Asn Glu Pro Glu Cys Gln Glu Ser Val Lys Ser Gln
            20                  25                  30

His Thr Glu Arg Cys Ile Asp
        35

<210> SEQ ID NO 10
<211> LENGTH: 39
<212> TYPE: PRT
<213> ORGANISM: C. elegans

<400> SEQUENCE: 10

Ala Lys Lys Leu Ser Lys Pro Asn Val Phe Ile Leu Asn Asn Arg Trp
1               5                   10                  15

Asp Ala Ser Ala Ala Glu Thr Glu Asn Ile Glu Asp Val Lys Lys Gln
            20                  25                  30

His Leu Thr Arg Phe Arg Gln
        35

<210> SEQ ID NO 11
<211> LENGTH: 39
<212> TYPE: PRT
<213> ORGANISM: Homo sapiens

<400> SEQUENCE: 11

Asn Glu Arg Leu Ser Lys Pro Asn Ile Phe Ile Leu Asn Asn Arg Trp
1               5                   10                  15

Asp Ala Ser Ala Ser Glu Pro Gly Tyr Met Glu Asp Val Arg Arg Gln
            20                  25                  30

His Met Glu Arg Cys Leu His
        35

<210> SEQ ID NO 12
<211> LENGTH: 39
<212> TYPE: PRT
<213> ORGANISM: M. musculus

<400> SEQUENCE: 12

Asn Glu Arg Leu Ser Lys Pro Asn Ile Phe Ile Leu Asn Asn Arg Trp
1               5                   10                  15

Asp Ala Ser Ala Ser Glu Pro Gly Tyr Met Glu Asp Val Arg Arg Gln
            20                  25                  30

His Met Glu Arg Cys Leu His
        35
```

```
<210> SEQ ID NO 13
<211> LENGTH: 21
<212> TYPE: PRT
<213> ORGANISM: Homo sapiens

<400> SEQUENCE: 13

Lys Ala Lys Leu Leu Arg Asn Lys Ala Gly Trp Leu Asp Ser Glu Leu
1               5                   10                  15

Asn Met Phe Thr His
            20

<210> SEQ ID NO 14
<211> LENGTH: 21
<212> TYPE: PRT
<213> ORGANISM: M. musculus

<400> SEQUENCE: 14

Arg Ala Lys Leu Leu Arg Asn Lys Ala Gly Trp Leu Asp Ser Glu Leu
1               5                   10                  15

Asn Met Phe Thr His
            20

<210> SEQ ID NO 15
<211> LENGTH: 21
<212> TYPE: PRT
<213> ORGANISM: D. melanogaster

<400> SEQUENCE: 15

Gln Leu Lys Leu Leu Arg Asn Lys Ala Asn Tyr Ile Gln Asn Glu Leu
1               5                   10                  15

Asp Ile Phe Glu His
            20

<210> SEQ ID NO 16
<211> LENGTH: 21
<212> TYPE: PRT
<213> ORGANISM: C. elegans

<400> SEQUENCE: 16

Thr Leu Gly Thr Ile Lys Gly Lys Ala Val Phe Leu Leu Arg Asn Leu
1               5                   10                  15

Glu Gln Phe Ala Ser
            20

<210> SEQ ID NO 17
<211> LENGTH: 21
<212> TYPE: PRT
<213> ORGANISM: Homo sapiens

<400> SEQUENCE: 17

Asn Ser Lys Leu Leu Arg Asn Lys Ala Val Gln Leu Glu Asn Glu Leu
1               5                   10                  15

Glu Asn Phe Thr Lys
            20

<210> SEQ ID NO 18
<211> LENGTH: 20
<212> TYPE: DNA
<213> ORGANISM: Artificial Sequence
<220> FEATURE:
<223> OTHER INFORMATION: nucleic acid primer

<400> SEQUENCE: 18
```

-continued tgcttcattc tcttggcagt          20

<210> SEQ ID NO 19
<211> LENGTH: 22
<212> TYPE: DNA
<213> ORGANISM: Artificial Sequence
<220> FEATURE:
<223> OTHER INFORMATION: nucleic acid primer

<400> SEQUENCE: 19
ggagtgcatt tctgcttggt ag        22

<210> SEQ ID NO 20
<211> LENGTH: 25
<212> TYPE: DNA
<213> ORGANISM: Artificial Sequence
<220> FEATURE:
<223> OTHER INFORMATION: nucleic acid primer

<400> SEQUENCE: 20
aacacttggc ttataccttt tctag     25

<210> SEQ ID NO 21
<211> LENGTH: 19
<212> TYPE: DNA
<213> ORGANISM: Artificial Sequence
<220> FEATURE:
<223> OTHER INFORMATION: nucleic acid primer

<400> SEQUENCE: 21
ccatgatgca gtgggagtc            19

<210> SEQ ID NO 22
<211> LENGTH: 19
<212> TYPE: DNA
<213> ORGANISM: Artificial Sequence
<220> FEATURE:
<223> OTHER INFORMATION: nucleic acid primer

<400> SEQUENCE: 22
gcttgactgc atcccagac            19

<210> SEQ ID NO 23
<211> LENGTH: 20
<212> TYPE: DNA
<213> ORGANISM: Artificial Sequence
<220> FEATURE:
<223> OTHER INFORMATION: nucleic acid primer

<400> SEQUENCE: 23
gcaactcccc aatacctcaa           20

<210> SEQ ID NO 24
<211> LENGTH: 20
<212> TYPE: DNA
<213> ORGANISM: Artificial Sequence
<220> FEATURE:
<223> OTHER INFORMATION: nucleic acid primer

<400> SEQUENCE: 24
gagacttgcc accagaggtc           20

<210> SEQ ID NO 25
<211> LENGTH: 20
<212> TYPE: DNA
<213> ORGANISM: Artificial Sequence

```
<220> FEATURE:
<223> OTHER INFORMATION: nucleic acid primer

<400> SEQUENCE: 25
tgattctccc caaagcattc                                               20

<210> SEQ ID NO 26
<211> LENGTH: 20
<212> TYPE: DNA
<213> ORGANISM: Artificial Sequence
<220> FEATURE:
<223> OTHER INFORMATION: nucleic acid primer

<400> SEQUENCE: 26
tatgacttcc ctgggagcag                                               20

<210> SEQ ID NO 27
<211> LENGTH: 20
<212> TYPE: DNA
<213> ORGANISM: Artificial Sequence
<220> FEATURE:
<223> OTHER INFORMATION: nucleic acid primer

<400> SEQUENCE: 27
atcttctacc agccgccatt                                               20

<210> SEQ ID NO 28
<211> LENGTH: 20
<212> TYPE: DNA
<213> ORGANISM: Artificial Sequence
<220> FEATURE:
<223> OTHER INFORMATION: nucleic acid primer

<400> SEQUENCE: 28
ggattgaaaa tgggtcacca                                               20

<210> SEQ ID NO 29
<211> LENGTH: 20
<212> TYPE: DNA
<213> ORGANISM: Artificial Sequence
<220> FEATURE:
<223> OTHER INFORMATION: nucleic acid primer

<400> SEQUENCE: 29
ccttccagac ttgggactgt                                               20

<210> SEQ ID NO 30
<211> LENGTH: 19
<212> TYPE: DNA
<213> ORGANISM: Artificial Sequence
<220> FEATURE:
<223> OTHER INFORMATION: nucleic acid primer

<400> SEQUENCE: 30
gcctggaacg ttctgtgac                                                19

<210> SEQ ID NO 31
<211> LENGTH: 20
<212> TYPE: DNA
<213> ORGANISM: Artificial Sequence
<220> FEATURE:
<223> OTHER INFORMATION: nucleic acid primer

<400> SEQUENCE: 31
actggcaaca ttgcactgaa                                               20
```

<210> SEQ ID NO 32
<211> LENGTH: 20
<212> TYPE: DNA
<213> ORGANISM: Artificial Sequence
<220> FEATURE:
<223> OTHER INFORMATION: nucleic acid primer

<400> SEQUENCE: 32
gtctcccatt cacctccaca                                               20

<210> SEQ ID NO 33
<211> LENGTH: 19
<212> TYPE: DNA
<213> ORGANISM: Artificial Sequence
<220> FEATURE:
<223> OTHER INFORMATION: nucleic acid primer

<400> SEQUENCE: 33
ccactgtgct gtgatgcag                                                19

<210> SEQ ID NO 34
<211> LENGTH: 20
<212> TYPE: DNA
<213> ORGANISM: Artificial Sequence
<220> FEATURE:
<223> OTHER INFORMATION: nucleic acid primer

<400> SEQUENCE: 34
agggaccctg gcctagatta                                               20

<210> SEQ ID NO 35
<211> LENGTH: 20
<212> TYPE: DNA
<213> ORGANISM: Artificial Sequence
<220> FEATURE:
<223> OTHER INFORMATION: nucleic acid primer

<400> SEQUENCE: 35
gtcccaggtc tgttctcagc                                               20

<210> SEQ ID NO 36
<211> LENGTH: 20
<212> TYPE: DNA
<213> ORGANISM: Artificial Sequence
<220> FEATURE:
<223> OTHER INFORMATION: nucleic acid primer

<400> SEQUENCE: 36
cactagatcc aggggtgcag                                               20

<210> SEQ ID NO 37
<211> LENGTH: 20
<212> TYPE: DNA
<213> ORGANISM: Artificial Sequence
<220> FEATURE:
<223> OTHER INFORMATION: nucleic acid primer

<400> SEQUENCE: 37
tcccaaagtg ctgggattac                                               20

<210> SEQ ID NO 38
<211> LENGTH: 20
<212> TYPE: DNA
<213> ORGANISM: Artificial Sequence
<220> FEATURE:
<223> OTHER INFORMATION: nucleic acid primer

<400> SEQUENCE: 38
tctcagcatc cccttctcag                                          20

<210> SEQ ID NO 39
<211> LENGTH: 20
<212> TYPE: DNA
<213> ORGANISM: Artificial Sequence
<220> FEATURE:
<223> OTHER INFORMATION: nucleic acid primer

<400> SEQUENCE: 39
ctgagaaggg gatgctgaga                                          20

<210> SEQ ID NO 40
<211> LENGTH: 20
<212> TYPE: DNA
<213> ORGANISM: Artificial Sequence
<220> FEATURE:
<223> OTHER INFORMATION: nucleic acid primer

<400> SEQUENCE: 40
tcactgcaga ctgggagatg                                          20

<210> SEQ ID NO 41
<211> LENGTH: 18
<212> TYPE: DNA
<213> ORGANISM: Artificial Sequence
<220> FEATURE:
<223> OTHER INFORMATION: nucleic acid primer

<400> SEQUENCE: 41
tctgtgcctc cccagctc                                            18

<210> SEQ ID NO 42
<211> LENGTH: 19
<212> TYPE: DNA
<213> ORGANISM: Artificial Sequence
<220> FEATURE:
<223> OTHER INFORMATION: nucleic acid primer

<400> SEQUENCE: 42
ggtggagcac ccttgtctc                                           19

<210> SEQ ID NO 43
<211> LENGTH: 20
<212> TYPE: DNA
<213> ORGANISM: Artificial Sequence
<220> FEATURE:
<223> OTHER INFORMATION: nucleic acid primer

<400> SEQUENCE: 43
atttctggca tccctcttg                                           20

<210> SEQ ID NO 44
<211> LENGTH: 21
<212> TYPE: DNA
<213> ORGANISM: Artificial Sequence
<220> FEATURE:
<223> OTHER INFORMATION: nucleic acid primer

<400> SEQUENCE: 44
tgaaaggctg agaagtccct a                                        21

<210> SEQ ID NO 45

<211> LENGTH: 21
<212> TYPE: DNA
<213> ORGANISM: Artificial Sequence
<220> FEATURE:
<223> OTHER INFORMATION: nucleic acid primer

<400> SEQUENCE: 45
gccatctgct aggatctctc c     21

<210> SEQ ID NO 46
<211> LENGTH: 23
<212> TYPE: DNA
<213> ORGANISM: Artificial Sequence
<220> FEATURE:
<223> OTHER INFORMATION: nucleic acid primer

<400> SEQUENCE: 46
tgtctctgtg gcttctactg tca     23

<210> SEQ ID NO 47
<211> LENGTH: 21
<212> TYPE: DNA
<213> ORGANISM: Artificial Sequence
<220> FEATURE:
<223> OTHER INFORMATION: nucleic acid primer

<400> SEQUENCE: 47
cccagcagtg acagtagaag c     21

<210> SEQ ID NO 48
<211> LENGTH: 22
<212> TYPE: DNA
<213> ORGANISM: Artificial Sequence
<220> FEATURE:
<223> OTHER INFORMATION: nucleic acid primer

<400> SEQUENCE: 48
ccagaacctg aaggtatcga gt     22

<210> SEQ ID NO 49
<211> LENGTH: 20
<212> TYPE: DNA
<213> ORGANISM: Artificial Sequence
<220> FEATURE:
<223> OTHER INFORMATION: nucleic acid primer

<400> SEQUENCE: 49
tggtagagcc ctgtctccaa     20

<210> SEQ ID NO 50
<211> LENGTH: 20
<212> TYPE: DNA
<213> ORGANISM: Artificial Sequence
<220> FEATURE:
<223> OTHER INFORMATION: nucleic acid primer

<400> SEQUENCE: 50
ttagggaacc cccgttttag     20

<210> SEQ ID NO 51
<211> LENGTH: 20
<212> TYPE: DNA
<213> ORGANISM: Artificial Sequence
<220> FEATURE:
<223> OTHER INFORMATION: nucleic acid primer

<400> SEQUENCE: 51
gagccactct gtgtccctgt                                          20

<210> SEQ ID NO 52
<211> LENGTH: 20
<212> TYPE: DNA
<213> ORGANISM: Artificial Sequence
<220> FEATURE:
<223> OTHER INFORMATION: nucleic acid primer

<400> SEQUENCE: 52
cagtggactg tggagtgtgg                                          20

<210> SEQ ID NO 53
<211> LENGTH: 20
<212> TYPE: DNA
<213> ORGANISM: Artificial Sequence
<220> FEATURE:
<223> OTHER INFORMATION: nucleic acid primer

<400> SEQUENCE: 53
gaaacatgaa ggctccttgg                                          20

<210> SEQ ID NO 54
<211> LENGTH: 20
<212> TYPE: DNA
<213> ORGANISM: Artificial Sequence
<220> FEATURE:
<223> OTHER INFORMATION: nucleic acid primer

<400> SEQUENCE: 54
agagagatgg ggaagggaga                                          20

<210> SEQ ID NO 55
<211> LENGTH: 20
<212> TYPE: DNA
<213> ORGANISM: Artificial Sequence
<220> FEATURE:
<223> OTHER INFORMATION: nucleic acid primer

<400> SEQUENCE: 55
aggagattct gccaaaccag                                          20

<210> SEQ ID NO 56
<211> LENGTH: 20
<212> TYPE: DNA
<213> ORGANISM: Artificial Sequence
<220> FEATURE:
<223> OTHER INFORMATION: nucleic acid primer

<400> SEQUENCE: 56
tttgtgtcca cacccaagac                                          20

<210> SEQ ID NO 57
<211> LENGTH: 20
<212> TYPE: DNA
<213> ORGANISM: Artificial Sequence
<220> FEATURE:
<223> OTHER INFORMATION: nucleic acid primer

<400> SEQUENCE: 57
ggtgtgtgtc aagcgtcctt                                          20

<210> SEQ ID NO 58
<211> LENGTH: 20
<212> TYPE: DNA

```
<213> ORGANISM: Artificial Sequence
<220> FEATURE:
<223> OTHER INFORMATION: nucleic acid primer

<400> SEQUENCE: 58
gatgaagcac tgagccaaca                                                 20

<210> SEQ ID NO 59
<211> LENGTH: 20
<212> TYPE: DNA
<213> ORGANISM: Artificial Sequence
<220> FEATURE:
<223> OTHER INFORMATION: nucleic acid primer

<400> SEQUENCE: 59
catgatgcct accctgtgaa                                                 20

<210> SEQ ID NO 60
<211> LENGTH: 22
<212> TYPE: DNA
<213> ORGANISM: Artificial Sequence
<220> FEATURE:
<223> OTHER INFORMATION: nucleic acid primer

<400> SEQUENCE: 60
ccagacaaaa cttgtcaatc ca                                              22

<210> SEQ ID NO 61
<211> LENGTH: 20
<212> TYPE: DNA
<213> ORGANISM: Artificial Sequence
<220> FEATURE:
<223> OTHER INFORMATION: nucleic acid primer

<400> SEQUENCE: 61
tgtgatgtgg cccaactcta                                                 20

<210> SEQ ID NO 62
<211> LENGTH: 20
<212> TYPE: DNA
<213> ORGANISM: Artificial Sequence
<220> FEATURE:
<223> OTHER INFORMATION: nucleic acid primer

<400> SEQUENCE: 62
gacacctgcc tctccacttc                                                 20

<210> SEQ ID NO 63
<211> LENGTH: 19
<212> TYPE: DNA
<213> ORGANISM: Artificial Sequence
<220> FEATURE:
<223> OTHER INFORMATION: nucleic acid primer

<400> SEQUENCE: 63
cgggagcagc aggtttact                                                  19

<210> SEQ ID NO 64
<211> LENGTH: 20
<212> TYPE: DNA
<213> ORGANISM: Artificial Sequence
<220> FEATURE:
<223> OTHER INFORMATION: nucleic acid primer

<400> SEQUENCE: 64
catggaggtc ctggatgtca                                                 20
```

```
<210> SEQ ID NO 65
<211> LENGTH: 20
<212> TYPE: DNA
<213> ORGANISM: Artificial Sequence
<220> FEATURE:
<223> OTHER INFORMATION: nucleic acid primer

<400> SEQUENCE: 65
ttgatgggct acaatgacca                                             20
```

METHODS OF DETECTING CHARCOT-MARIE TOOTH DISEASE TYPE 2A

RELATED APPLICATION

This application claims the benefit of U.S. Provisional Application No. 60/520,429, filed on Nov. 14, 2003. The entire teachings of the above application are incorporated herein by reference.

GOVERNMENT SUPPORT

The invention was supported, in whole or in part, by grants 2P01-NS26630-14 and 2R01-NS29416-09 from the National Institutes of Health. The Government has certain rights in the invention.

BACKGROUND OF THE INVENTION

Charcot-Marie-Tooth (CMT) neuropathy, also known as hereditary motor and sensory neuropathy, is a heterogeneous group of inherited diseases of peripheral nerves. CMT is a common disorder affecting both children and adults. CMT causes significant neuromuscular impairment. It is estimated that 1/2500 persons have a form of CMT, making it one of the largest categories of genetic diseases.

CMT comprises a frequently occurring, genetically heterogeneous group of peripheral neuropathies, although the clinical picture is rather uniform. See, Vance et al., The many faces of Charcot-Marie-Tooth disease. *Arch Neurol* 57, 638-640 (2000). Following electrophysiological criteria, CMT falls into two major forms, the demyelinating CMT type 1 with decreased nerve conduction velocities (NCV), and the axonal form, CMT type 2. In contrast to the well known molecular genetic defects causing the CMT1 phenotype, several genes underlying CMT2 have only recently been identified. So far, seven loci for autosomal dominant CMT2 have been assigned to chromosomes 1p35-36 (CMT2A), 3q13-22 (CMT2B), 12q23-24 (CMT2C), 7p14 (CMT2D), 8p21 (CMT2E), 7q11-21 (CMT2F), and 12q12-13.3 (CMT2G). See, e.g., Ben Othmane et al., Localization of a gene (CMT2A) for autosomal dominant Charcot-Marie-Tooth disease type 2 to chromosome 1p and evidence of genetic heterogeneity. *Genomics* 17, 370-375 (1993); Kwon et al., Assignment of a second Charcot-Marie-Tooth type II locus to chromosome 3q. *Am J Hum Genet* 57, 853-858 (1995); Klein et al., The gene for HMSN2C maps to 12q23-24: a region of neuromuscular disorders. *Neurology* 60, 1151-1156 (2003); Ionasescu et al., Autosomal dominant Charcot-Marie-Tooth axonal neuropathy mapped on chromosome 7p (CMT2D). *Hum Mol Genet* 5, 1373-1375 (1996); Mersiyanova et al., A new variant of Charcot-Marie-Tooth disease type 2 is probably the result of a mutation in the neurofilament-light gene. *Am J Hum Genet* 67, 37-46 (2000); Ismailov et al., A new locus for autosomal dominant Charcot-Marie-Tooth disease type 2 (CMT2F) maps to chromosome 7ql1-q21. *Eur J Hum Genet* 9, 646-650 (2001).

Currently four genes, involved in CMT2A, CMT2B, CMT2D and CMT2E, have been identified. The neurofilament-light gene (NEFL) is responsible for CMT2E, and a large study revealed that NEFL mutations occur in only 2% of CMT patients. See, Jordanova et al., Mutations in the neurofilament light chain gene (NEFL) cause early onset severe Charcot-Marie-Tooth disease, *Brain* 126, 590-597 (2003). Two missense mutations in the RAS-related late-endosomal GTP-binding protein RAB7 have been shown to cause CMT2B in 3 extended families and 2 familial cases with different ethnic backgrounds. See, Verhoeven et al., Mutations in the small GTP-ase late endosomal protein RAB7 cause Charcot-Marie-Tooth type 2B neuropathy. *Am J Hum Genet* 72, 722-727 (2003). Missense mutations in the gene coding for Glycyl tRNA synthetase (GARS) were reported to cause CMT2D and distal hereditary motor neuropathy type VII in different families. Antonellis et al., Glycyl tRNA Synthetase Mutations in Charcot-Marie-Tooth Disease Type 2D and Distal Spinal Muscular Atrophy Type V. *Am J Hum Genet* 72, 1293-1299 (2003).

In a single Japanese family with a posterior probability supporting linkage to the CMT2A locus, a missense mutation in the KIF1B-β gene (c.293A>T; Gln98Leu) was found to co-segregate with the disease. Zhao et al., Charcot-Marie-Tooth disease type 2A caused by mutation in a microtubule motor KIF1Bb. *Cell* 105, 587-597 (2001). The Leu98 allele was not found in 95 healthy control individuals. In addition, the authors of this study demonstrated that Kif1B$^{+/-}$mice developed a chronic peripheral neuropathy resembling the CMT phenotype in humans. Zhao et al. 2001. Yet, no further CMT2A families have been reported with a mutation in KIF1B-β. Therefore, it may be desirable to find a different method of diagnosing Charcot-Marie-Tooth disease.

SUMMARY OF THE INVENTION

The present invention includes a method of screening a subject for risk of Charcot-Marie-Tooth Disease Type 2A comprising detecting the presence or absence of a mutation in the mitofusin gene in a biological sample collected from the subject; and determining if the subject is at an increased or decreased risk of Charcot-Marie-Tooth Disease Type 2A due to the presence of the mutation in the mitofusin gene. The present invention also includes methods for detecting the presence of a genetic polymorphism associated with Charcot-Marie-Tooth Disease Type 2A in a sample of patient nucleic acid, comprising amplifying a mitofusin gene sequence in the patient nucleic acid to produce an amplification product; and identifying the presence of a Charcot-Marie-Tooth Disease Type 2A associated polymorphism in the amplification product. The present invention also include methods of diagnosing Charcot-Marie-Tooth Disease or a genetic predisposition for developing Charcot-Marie-Tooth Disease in a subject, comprising providing a biological sample from the subject wherein said sample comprises a mitofusin gene; detecting one or more mutations in the mitofusin gene; and determining that the subject has at least one detected mutation in at least one genomic copy of the mitofusin gene, wherein the presence of at least one detected mutation in the mitofusin gene is diagnostic for Charcot-Marie-Tooth Disease or a genetic predisposition for developing Charcot-Marie-Tooth Disease in the subject.

BRIEF DESCRIPTION OF THE DRAWINGS

FIG. 1A illustrates the physical map with the contiguous NT_021937 containing KIF1B, typical STR markers, and the screened genes including MFN2. The CMT2A locus is defined by the markers D1S160 and D1S434. FIG. 1B depicts the genomic structure of MFN2 with six detected unique mutations within functional domains (white bars); translated mRNA (black bars), untranslated mRNA and alternative spliced exons (grey bars); tel: telomeric; cen: centromeric; TM: transmembrane domain; Cc: coiled-coil.

FIG. 3A illustrate three different missense mutations were identified at the beginning of the GTPase domain. The broken line corresponds to the GTPase starting point. Sequences include those from *H. sapiens* Mfn2 (SEQ ID NO:1); *M. musculus* Mfn2 (SEQ ID NO:2); *D. melanogaster* (SEQ ID NO:3); *C. elegans* Mnf2 (SEQ ID NO:4); *H. sapiens* Mfn1 (SEQ ID NO:5); and *M. musculus* Mfn1 (SEQ ID NO:6). FIG. 3B depicts two conserved missense mutations in the GTPase domain. Sequences include those from *H. sapiens* Mfn2 (SEQ ID NO:7); *M. musculus* Mfn2 (SEQ ID NO:8); *D. melanogaster* (SEQ ID NO:9); *C. elegans* Mnf2 (SEQ ID NO:10); *H. sapiens* Mfn1 (SEQ ID NO:11); and *M. musculus* Mfn1 (SEQ ID NO:12). FIG. 3C shows a missense mutation occurred at the end of the fzo_mitofusin domain. The black background for this figure indicates highly conserved amino acids. The scale orientates on the human MFN2 protein sequence (NM_014874). Sequences include those from *H. sapiens* Mfn2 (SEQ ID NO:13); *M. musculus* Mfn2 (SEQ ID NO:14); *D. melanogaster* (SEQ ID NO:15); *C. elegans* Mnf2 (SEQ ID NO:16); and *H. sapiens* Mfn1 (SEQ ID NO:17).

DETAILED DESCRIPTION OF THE INVENTION

The present invention provides methods of screening (e.g., diagnosing or prognosing) for diseases, such as Charcot-Marie-Tooth Disease in a subject. The present invention relates to methods for the genetic diagnosis of Charcot-Marie-Tooth Disease as well as to probes for the genetic diagnosis of Charcot-Marie-Tooth Disease. Embodiments of the present invention are also directed to detecting the presence or absence of genetic polymorphisms in genes relating to Charcot-Marie-Tooth Disease. The present invention relates to data excluding mutations in the KIF1B gene in six CMT2A families. The lack of KIF1B mutations in these families illustrate genetic heterogeneity at the CMT2A locus.

Figure 1A:
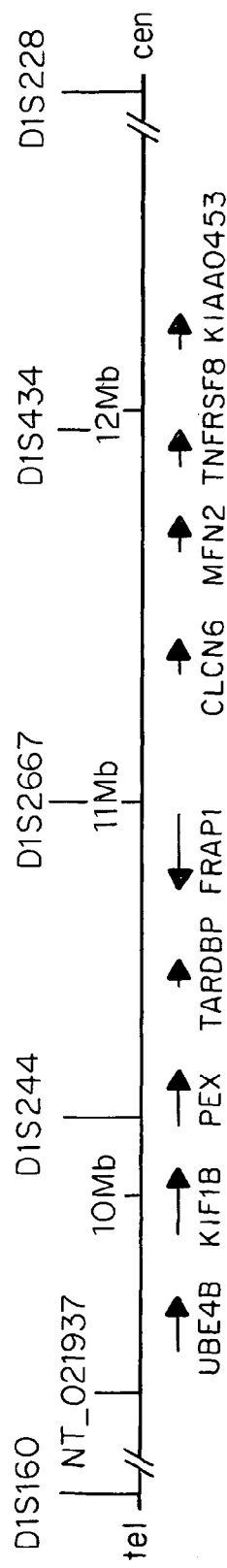
FIGS. 1A-1B illustrate a transcript map of the CMT2A region on chromosome 1p35.2.

One of the embodiments of the present invention includes a method of screening a subject for risk of Charcot-Marie-Tooth Disease Type 2A comprising detecting the presence or absence of a mutation in the mitofusin gene in a biological sample collected from the subject. Detecting the presence or absence of a mutation in the mitofu sin gene can assist in determining if the subject is at an increased or decreased risk of Charcot-Marie-Tooth Disease Type 2A due to the presence of the mutation in the mitofusin gene. The detecting step can test for homozygous or heterozygous mutations. The biological sample can include both nucleic and amino acids. The sample can also include a chromosomal nucleic acid. The chromosomal nucleic acid can be Chromosome 1 or a fragment thereof. Additional these fragments can include chromosome 1p36 and fragments thereof of this fragment. The chromosomal nucleic acid can further be defined as being located within the markers D1S160 and D1S434 (FIG. 1A). The mutation detected can occur any position in a mitofusin gene. These different mutations can include both missense and nonsense mutations and can be located in the gene Mitofusin 2 (MFN2), which is located 1.65 Mb downstream from the KIF1B locus on chromosome 1p36 (FIG. 1). Some of the embodiments of the present invention include mutations at positions selected from the group consisting of 2219, 839, 751, 493, 281, 227 and 205 in a nucleic acid sequence of a mitofusin 2 (gene accession number AAH17061, incorporated by reference). Those skilled in the art will appreciate that similar deletions can be made in the homologous regions of other mitofusin genes, such as mitofusin 1, accession number AAH40557, incorporated by reference. These mutations for mitofusin 2 can change the nucleic acid sequence as follows: 2219G>C, 839G>A, 751C>G, 493 C>G, 281G>A, 227T>C and 205G>T. Additional mutations may be located applying the algorithm by Lupas et al., Predicting coiled coils from protein sequences. *Science* 252, 1162-1164 (1991). Thus, one of skill in the art could determine that a change in the amino acid sequence could extend the coiled-coil structure that occurs at the end of the fzo_mitofusin domain which would indicate Charcot-Marie-Tooth Disease. Additionally, one of skill in the art can determine a homologous region of a mitofusin gene similar to the mutations of the mitofusin 2 gene.

Embodiments of the present invention also include amino acid mutations caused by mutations in the nucleic acid sequence. These mutations can occur at positions 740, 280, 251, 165, 76 and 69 in an amino acid sequence of a mitofusin 2 gene, or a homologous region of a mitofusin gene. The mutations are based upon the nucleic acid mutations discussed above. These mutations can result in a missense mutation which causes an amino acid mutation. In particular embodiments, these mutations can result in the following changes: 740Trp>Ser; 280Arg>His; 251Pro>Ala, 165His>Asp, 76Leu>Pro and 69Val>Phe.

Another embodiment of the present invention includes a method for detecting the presence of a genetic polymorphism associated with Charcot-Marie-Tooth Disease Type 2A in a sample of a patient's nucleic acid. This method can comprise amplifying a mitofusin gene sequence in the patient nucleic acid to produce an amplification product, and identifying the presence of a Charcot-Marie-Tooth Disease Type 2A associated polymorphism in the amplification product. The polymorphism can be identified by sequencing the amplification product. Additionally, the amplification product can be digested with a restriction enzyme so that the Charcot-Marie-Tooth Disease Type 2A polymorphism is identified by sequencing a restriction fragment.

Embodiments of the present invention can also include methods of diagnosing Charcot-Marie-Tooth Disease or a genetic predisposition for developing Charcot-Marie-Tooth Disease in a subject. These methods can include providing a mitofusin gene from the subject, detecting one or more mutations in the biological sample, and determining that the subject has at least one detected mutation in at least genomic copy of the mitofusin gene. Thus, a test can be performed to determine if the subject is homozygous or heterozygous for Charcot-Marie-Tooth Disease. The presence of at least one detected mutation in at least copy of the sequence encoding the mitofusin gene is diagnostic for Charcot-Marie-Tooth Disease or a genetic predisposition for developing Charcot-Marie-Tooth Disease in a subject or the subject's offspring.

Figure 3A:
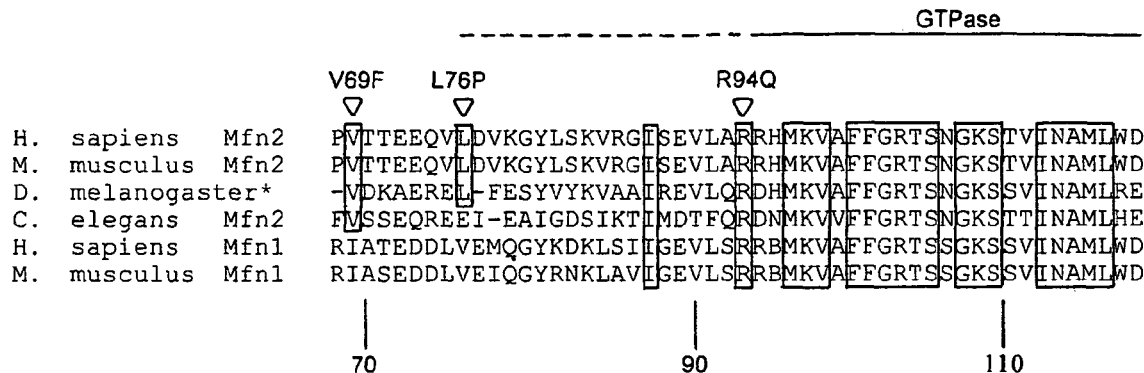
FIGs. 3A-3C illustrates the sequence conservation of MFN2 and MFN1 in different species related to predicted domains. The sites of the identified mutations in CMT2A families are indicated by triangles.
Figure 3B:
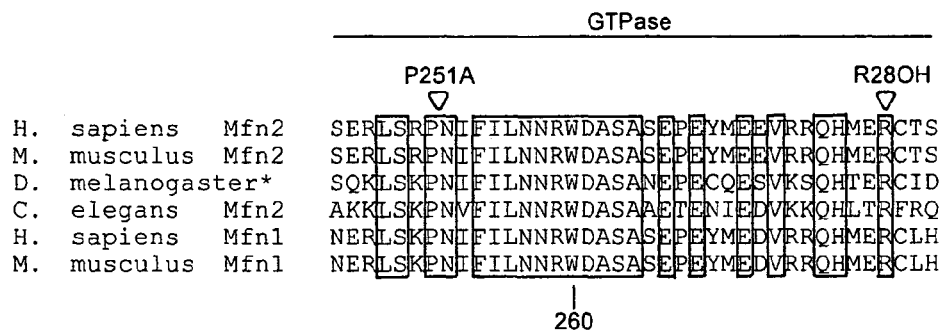
Figure 3C:
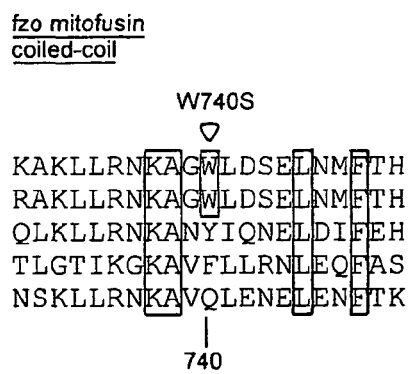

Mutations in MFN2 represent the major gene locus for the Charcot-Marie-Tooth neuropathy type 2A. The MFNs, which reside at the outer mitochondrial membrane, have been shown to regulate the mitochondrial network architecture by the fusion of mitochondria. Mitochondria represent a tubular and branched membrane network, which undergoes a dynamically regulated balance between fusion and fission reactions. MFN2 has one human homologue, MFN1, and highly conserved members in different species, including *Caenorhabditis elegans* and the fuzzy onions (Fzo) gene in *Drosophila melanogaster* (FIG. 3).

Figure 1B:
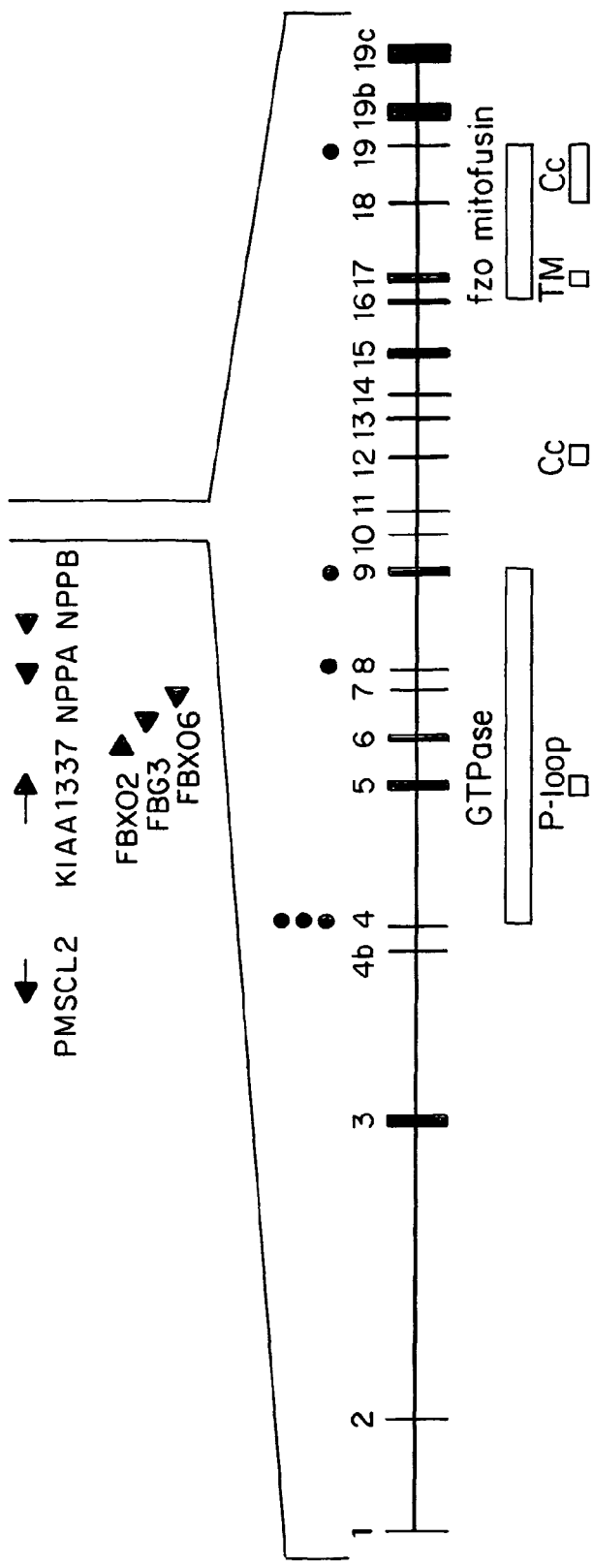
Figure 2A:
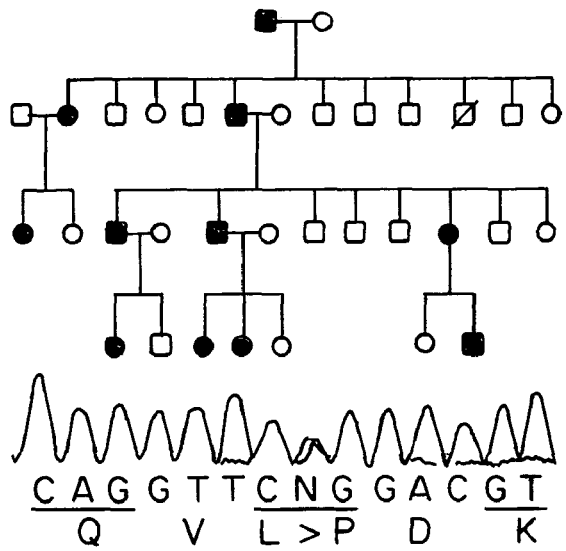
FIGS. 2A-2E illustrates the pedigrees and detected mutations in five CMT2A families.
Figure 2B:
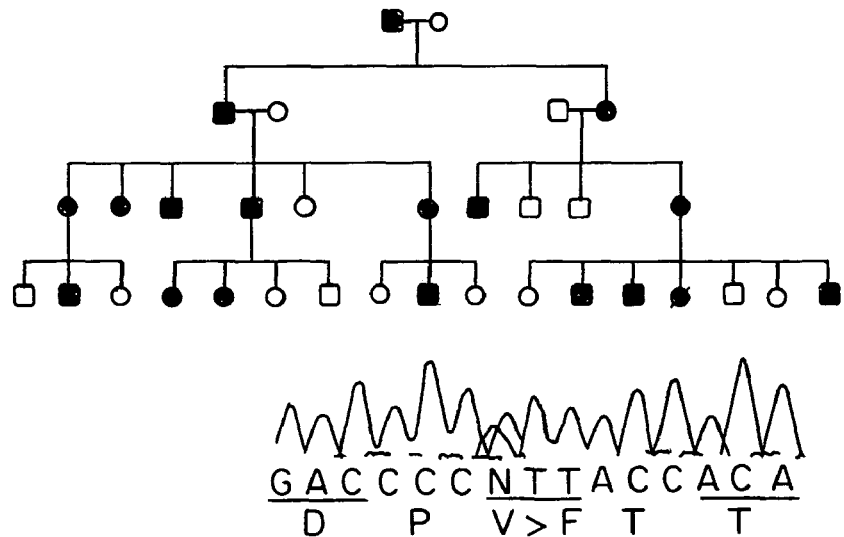
Figure 2C:
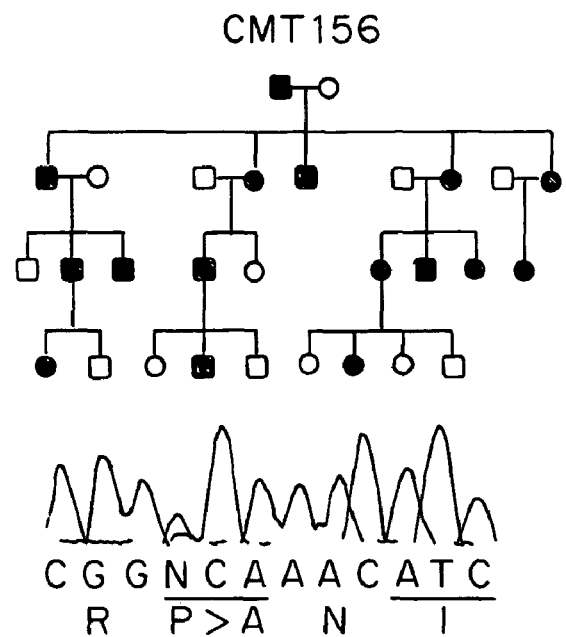
Figure 2D:
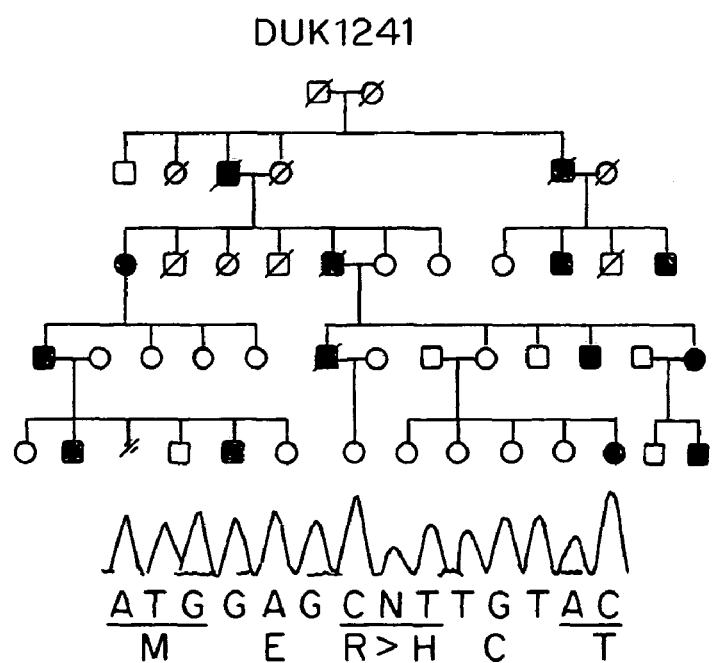
Figure 2E:
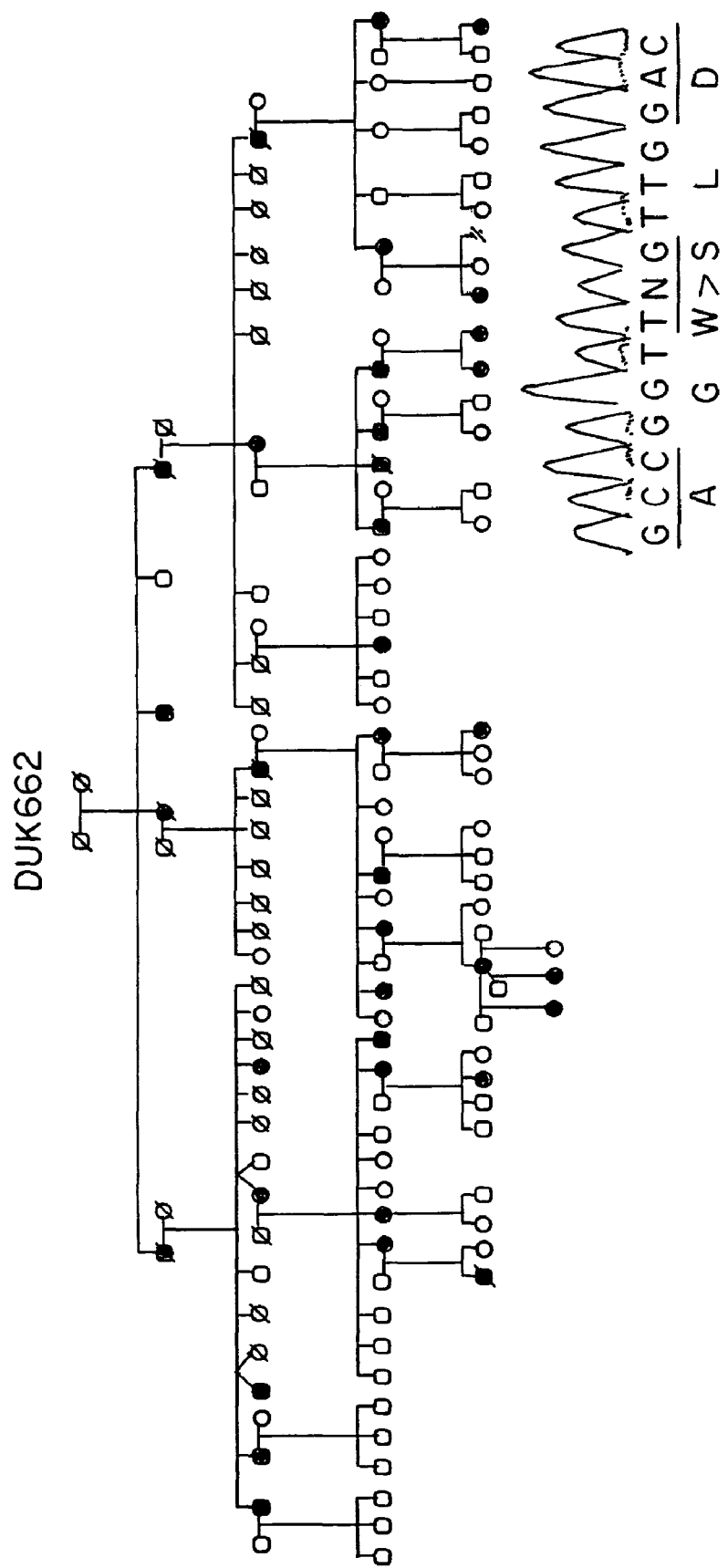

The majority of the identified mutations in CMT2A families were in exons 4, 8, and 9 and related to the GTPase domain (FIG. 1B), which has been shown to be essential for the mitochondrial fusion activity of Mfn2. See, Santel et al., Control of mitochondrial morphology by a human mitofusin. *J Cell Sci* 114, 867-874 (2001); Hales et al., Developmentally regulated mitochondrial fusion mediated by a conserved, novel, predicted GTPase. *Cell* 90, 121-129 (1997); and Hermann et al., Mitochondrial fusion in yeast requires the transmembrane GTPase Fzo1p. *J Cell Biol* 143, 359-373 (1998). The affected amino acids were conserved in various species (FIG. 3). Analysis of MFN2 by PSORT and MITOPROT revealed a mitochondrial targeting signal at the N-terminal site, thus the detected mutations in CMT2A families V69F, L76P, and R94Q can modulate mitochondrial targeting. One mutation occurred in the fzo_mitofusin domain in exon 19 (FIG. 1B). This mutation can extend the C-terminal coiled-coil domain, which is required for efficient mitochondrial targeting.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety. "Functional polymorphism" as used herein refers to a change in the base pair sequence of a gene that produces a qualitative or quantitative change in the activity of the protein encoded by that gene (e.g., a change in specificity of activity; a change in level of activity). The presence of a functional polymorphism indicates that the subject is at greater risk of developing a particular disease as compared to the general population. For example, the patient carrying the functional polymorphism may be particularly susceptible to chronic exposure to environmental toxins that contribute to Charcot-Marie-Tooth Disease. The term "functional polymorphism" includes mutations, deletions and insertions.

The term "Mutation" as used herein sometimes refers to a functional polymorphism that occurs in less than five percent of the population, and is strongly correlated to the presence of a gene (i.e., the presence of such mutation indicating a high risk of the subject being afflicted with a disease). However, "mutation" is also used herein to refer to a specific site and type of functional polymorphism, without reference to the degree of risk that particular mutation poses to an individual for a particular disease.

Subjects for screening and/or treatment with the present invention are, in general, human subjects, including both female and male subjects. The subject may be of any race and any age, including juvenile, adolescent, and adult. It will be appreciated by those skilled in the art that, while the present methods are useful for screening subjects to provide an initial indication of the suitability of a patient for a particular treatment, this information will typically be considered by a clinician or medical practitioner in light of other factors and experience in reaching a final judgment as to the treatment which any given subject should receive.

Suitable subjects include those who have not previously been diagnosed as afflicted with Charcot-Marie-Tooth Disease, those who have previously been determined to be at risk of developing Charcot-Marie-Tooth Disease, and those who have been initially diagnosed as being afflicted with Charcot-Marie-Tooth Disease where confirming information is desired. Thus, it is contemplated that the methods described herein be used in conjunction with other clinical diagnostic information known or described in the art which are used in evaluation of subjects with Charcot-Marie-Tooth Disease or suspected to be at risk for developing such disease.

The detecting step may be carried out in accordance with known techniques, such as by collecting a biological sample containing DNA from the subject, and then determining the presence or absence of DNA encoding or indicative of the mutation in the biological sample. Any biological sample which contains the DNA of that subject may be employed, including tissue samples and blood samples, with blood cells being a particularly convenient source.

In general, the step of detecting the polymorphism of interest may be carried out by collecting a biological sample containing DNA from the subject, and then determining the presence or absence of DNA containing the polymorphism of interest in the biological sample. Any biological sample which contains the DNA of that subject may be employed, including tissue samples and blood samples, with blood cells being a particularly convenient source. The nucleotide sequence of the mitofusin gene is known and suitable probes, restriction enzyme digestion techniques, or other means of detecting the polymorphism may be implemented based on this known sequence in accordance with standard techniques. See, e.g., U.S. Pat. Nos. 6,027,896 and 5,767,248 to A. Roses et al. (Applicants specifically intend that the disclosures of all United States patent references cited herein be incorporated by reference herein in their entirety).

Determining the presence or absence of DNA encoding a particular mutation may be carried out with an oligonucleotide probe labeled with a suitable detectable group, and/or by means of an amplification reaction such as a polymerase chain reaction or ligase chain reaction (the product of which amplification reaction may then be detected with a labeled oligonucleotide probe or a number of other techniques). Further, the detecting step may include the step of detecting whether the subject is heterozygous or homozygous for the particular mutation. Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al. (applicants specifically intend that the disclosures of all U.S. Patent references cited herein be incorporated herein by reference).

Amplification of a selected, or target, nucleic acid sequence may be carried out by any suitable means. See generally, Kwoh et al., *Am. Biotechnol. Lab.* 8, 14-25 (1990). Examples of suitable amplification techniques include, but are not limited to, polymerase chain reaction, ligase chain reaction, strand displacement amplification (see generally G. Walker et al., *Proc. Natl. Acad. Sci. USA* 89, 392-396 (1992); G. Walker et al., *Nucleic Acids Res.* 20, 1691-1696 (1992)), transcription-based amplification (see D. Kwoh et al., *Proc. Natl. Acad Sci. USA* 86, 1173-1177 (1989)), self-sustained sequence replication (or "3SR") (see J. Guatelli et al., *Proc. Natl. Acad. Sci. USA* 87, 1874-1878 (1990)), the Qβ replicase system (see P. Lizardi et al., BioTechnology 6, 1197-1202 (1988)), nucleic acid sequence-based amplification (or "NASBA") (see R. Lewis, *Genetic Engineering News* 12 (9), 1 (1992)), the repair chain reaction (or "RCR") (see R. Lewis, supra), and boomerang DNA amplification (or "BDA") (see R. Lewis, supra). Polymerase chain reaction is particularly used.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. When PCR conditions allow for amplification of all allelic types, the types can be distinguished by hybridization with an allelic specific probe, by restriction endonuclease digestion, by electrophoresis on denaturing gradient gels, or other techniques.

Ligase chain reaction (LCR) is also carried out in accordance with known techniques. See, e.g., R. Weiss, *Science* 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

DNA amplification techniques such as the foregoing can involve the use of a probe, a pair of probes, or two pairs of probes which specifically bind to DNA containing the functional polymorphism, but do not bind to DNA that does not contain the functional polymorphism. Alternatively, the probe or pair of probes could bind to DNA that both does and does not contain the functional polymorphism, but produce or amplify a product (e.g., an elongation product) in which a detectable difference may be ascertained (e.g., a shorter product, where the functional polymorphism is a deletion mutation). Such probes can be generated in accordance with standard techniques from the known sequences of DNA in or associated with a gene linked to Charcot-Marie-Tooth Disease or from sequences which can be generated from such genes in accordance with standard techniques.

It will be appreciated that the detecting steps described herein may be carried out directly or indirectly. Other means of indirectly determining allelic type include measuring polymorphic markers that are linked to the particular functional polymorphism, as has been demonstrated for the VNTR (variable number tandem repeats).

Kits for determining if a subject is or was (in the case of deceased subjects) afflicted with or is or was at increased risk of developing Charcot-Marie-Tooth Disease will include at least one reagent specific for detecting for the presence or absence of at least one functional polymorphism as described herein and instructions for observing that the subject is or was afflicted with or is or was at increased risk of developing Charcot-Marie-Tooth Disease if at least one of the functional polymorphisms is detected. The kit may optionally include one or more nucleic acid probes for the amplification and/or detection of the functional polymorphism by any of the techniques described above, with PCR being currently utilized.

Molecular biology comprises a wide variety of techniques for the analysis of nucleic acid and protein sequences. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, Molecular Cloning: A Laboratory Manual, 2 Ed., Cold spring Harbor Laboratory Press, Cold Spring Harbor, N.Y., 1989).

Most of these techniques involve carrying out numerous operations (e.g., pipetting, centrifugation, and electrophoresis) on a large number of samples. They are often complex and time consuming, and generally require a high degree of accuracy. Many a technique is limited in its application by a lack of sensitivity, specificity, or reproducibility.

For example, the complete process for carrying out a DNA hybridization analysis for a genetic or infectious disease is very involved. Broadly speaking, the complete process may be divided into a number of steps and sub-steps. In the case of genetic disease diagnosis, the first step involves obtaining the sample (e.g., saliva, blood or tissue). Depending on the type of sample, various pre-treatments would be carried out. The second step involves disrupting or lysing the cells which releases the crude DNA material along with other cellular constituents.

Generally, several sub-steps are necessary to remove cell debris and to further purify the DNA from the crude sample. At this point several options exist for further processing and analysis. One option involves denaturing the DNA and carrying out a direct hybridization analysis in one of many formats (dot blot, microbead, microplate, etc.). A second option, called Southern blot hybridization, involves cleaving the DNA with restriction enzymes, separating the DNA fragments on an electrophoretic gel, blotting the DNA to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out an amplification procedure such as the polymerase chain reaction (PCR) or the strand displacement amplification (SDA) method. These procedures amplify (increase) the number of target DNA sequences relative to non-target sequences. Amplification of target DNA helps to overcome problems related to complexity and sensitivity in genomic DNA analysis. After these sample preparation and DNA processing steps, the actual hybridization reaction is performed. Finally, detection and data analysis convert the hybridization event into an analytical result.

Nucleic acid hybridization analysis generally involves the detection of a very small number of specific target nucleic acids (DNA or RNA) with an excess of probe DNA, among a relatively large amount of complex non-target nucleic acids. A reduction in the complexity of the nucleic acid in a sample is helpful to the detection of low copy numbers (i.e. 10,000 to 100,000) of nucleic acid targets. DNA complexity reduction is achieved to some degree by amplification of target nucleic acid sequences. (See, M. A. Innis et al., PCR Protocols: A Guide to Methods and Applications, Academic Press, 1990, Spargo et al., 1996, Molecular & Cellular Probes, in regard to SDA amplification). This is because amplification of target nucleic acids results in an enormous number of target nucleic acid sequences relative to non-target sequences thereby improving the subsequent target hybridization step.

The actual hybridization reaction represents one of the most important and central steps in the whole process. The hybridization step involves placing the prepared DNA sample in contact with a specific reporter probe at set optimal conditions for hybridization to occur between the target DNA sequence and probe.

Hybridization may be performed in any one of a number of formats. For example, multiple sample nucleic acid hybridization analysis has been conducted in a variety of filter and solid support formats (See Beltz et al., *Methods in Enzymology*, Vol. 100, Part et al., Eds., Academic Press, New York, Chapter 19, pp. 266-308, 1985). One format, the so-called "dot blot" hybridization, involves the non-covalent attachment of target DNAs to a filter followed by the subsequent hybridization to a radioisotope labeled probe(s). "Dot blot" hybridization gained wide-spread use over the past two decades during which time many versions were developed (see Anderson and Young, in Nucleic Acid Hybridization—A Practical Approach, Hames and Higgins, Eds., IRL Press, Washington, D.C. Chapter 4, pp. 73-111, 1985). For example, the dot blot method has been developed for multiple analyses of genomic mutations (EPA 0228075 to Nanibhushan et al.) and for the detection of overlapping clones and the construction of genomic maps (U.S. Pat. No. 5,219,726 to Evans).

Additional techniques for carrying out multiple sample nucleic acid hybridization analysis include micro-formatted multiplex or matrix devices (e.g., DNA chips) (see M. Barinaga, 253 *Science*, pp. 1489, 1991; W. Bains, 10 *Bio/Technology*, pp. 757-758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 5 Bio/Technology, pp. 757-758, 1992). SBH makes use of all possible n-nucleotide oligomers (n-mers) to identify n-mers in an unknown DNA sample, which are subsequently aligned by algorithm analysis to produce the DNA sequence (See, Drmanac U.S. Pat. No. 5,202,231).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, (United Kingdom Patent Application GB 8810400, 1988; E. M. Southern et al., 13 Genomics 1008, 1992), proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency conditions for each oligonucleotide on an array.

Drmanac et al., (260 Science 1649-1652, 1993), used the second format to sequence several short (116 bp) DNA sequences. Target DNAs were attached to membrane supports ("dot blot" format). Each filter was sequentially hybridized with 272 labeled 10-mer and 11-mer oligonucleotides. Wide ranges of stringency conditions were used to achieve specific hybridization for each n-mer probe. Washing times varied from 5 minutes to overnight using temperatures from 0° C. to 16° C. Most probes required 3 hours of washing at 16° C. The filters had to be exposed from 2 to 18 hours in order to detect hybridization signals. The overall false positive hybridization rate was 5% in spite of the simple target sequences, the reduced set of oligomer probes, and the use of the most stringent conditions available.

Currently, a variety of methods are available for detection and analysis of the hybridization events. Depending on the reporter group (fluorophore, enzyme, radioisotope, etc.) used to label the DNA probe, detection and analysis are carried out fluorimetrically, calorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. Thus, detection of hybridization events is dependent upon how specific and sensitive hybridization can be made. Concerning genetic analysis, several methods have been developed that have attempted to increase specificity and sensitivity.

One form of genetic analysis is analysis centered on elucidation of single nucleic acid polymorphisms or ("SNPs"). Factors favoring the usage of SNPs are their high abundance in the human genome (especially compared to short tandem repeats, (STRs)), their frequent location within coding or regulatory regions of genes (which can affect protein structure or expression levels), and their stability when passed from one generation to the next (Landegren et al., Genome Research, Vol. 8, pp. 769-776, 1998).

A SNP is defined as any position in the genome that exists in two variants and the most common variant occurs less than 99% of the time. In order to use SNPs as widespread genetic markers, it is crucial to be able to genotype them easily, quickly, accurately, and cost-effectively. It is of great interest to type both large sets of SNPs in order to investigate complex disorders where many loci factor into one disease (Risch and Merikangas, Science, Vol. 273, pp. 1516-1517, 1996), as well as small subsets of SNPs previously demonstrated to be associated with known afflictions.

Numerous techniques are currently available for typing SNPs (for review, see Landegren et al., Genome Research, Vol. 8, pp. 769-776, (1998), all of which require target amplification. They include direct sequencing (Carothers et al., *BioTechniques,* Vol. 7, pp. 494-499, 1989), single-strand conformation polymorphism (Orita et al., *Proc. Natl. Acad. Sci. USA*, Vol. 86, pp. 2766-2770, 1989), allele-specific amplification (Newton et al., *Nucleic Acids Research*, Vol. 17, pp. 2503-2516, (1989), restriction digestion (Day and Humphries, *Analytical Biochemistry*, Vol. 222, pp. 389-395, 1994), and hybridization assays. In their most basic form, hybridization assays function by discriminating short oligonucleotide reporters against matched and mismatched targets. Many adaptations to the basic protocol have been developed. These include ligation chain reaction (Wu and Wallace, *Gene, Vol.* 76, pp. 245-254, 1989) and minisequencing (Syvanen et al., *Genomics*, Vol. 8, pp. 684-692, 1990). Other enhancements include the use of the 5'-nuclease activity of Taq DNA polymerase (Holland et al., *Proc. Natl. Acad. Sci. USA*, Vol. 88, pp. 7276-7280, 1991), molecular beacons (Tyagi and Kramer, *Nature Biotechnology*, Vol. 14, pp.303-308, 1996), heat denaturation curves (Howell et al., *Nature Biotechnology*, Vol. 17, pp. 87-88, 1999) and DNA "chips" (Wang et al., *Science*, Vol. 280, pp. 1077-1082, 1998).

An additional phenomenon that can be used to distinguish SNPs is the nucleic acid interaction energies or base-stacking energies derived from the hybridization of multiple target specific probes to a single target. (see R. Ornstein et al., "An Optimized Potential Function for the Calculation of Nucleic Acid Interaction Energies", *Biopolymers*, Vol.17, 2341-2360 (1978); J. Norberg and L. Nilsson, *Biophysical Journal*, Vol. 74, pp. 394-402, (1998); and J. Pieters et al., *Nucleic Acids Research*, Vol.17, no. 12, pp. 4551-4565 (1989)). This base-stacking phenomenon is used in a unique format in the current invention to provide highly sensitive Tm differentials allowing the direct detection of SNPs in a nucleic acid sample.

Additional methods have been used to distinguish nucleic acid sequences in related organisms or to sequence DNA. For example, U.S. Pat. No. 5,030,557 by Hogan et al. disclosed that the secondary and tertiary structure of a single stranded target nucleic acid may be affected by binding "helper" oligonucleotides in addition to "probe" oligonucleotides causing a higher Tm to be exhibited between the probe and target nucleic acid. That application however was limited in its approach to using hybridization energies only for altering the secondary and tertiary structure of self-annealing RNA strands which if left unaltered would tend to prevent the probe from hybridizing to the target.

With regard to DNA sequencing, K. Khrapko et al., Federation of European *Biochemical Societies Letters*, Vol. 256, no. 1,2, pp. 118-122 (1989), for example, disclosed that continuous stacking hybridization resulted in duplex stabilization. Additionally, J. Kieleczawa et al., *Science*, Vol. 258, pp. 1787-1791 (1992), disclosed the use of contiguous strings of hexamers to prime DNA synthesis wherein the contiguous strings appeared to stabilize priming. Likewise, L. Kotler et al., *Proc. Natl. Acad. Sci.* USA, Vol. 90, pp. 4241-4245, (1993) disclosed sequence specificity in the priming of DNA sequencing reactions by use of hexamer and pentamer oligonucleotide modules; Further, S. Parinov et al., *Nucleic Acids Research*, Vol. 24, no. 15, pp. 2998-3004, (1996), disclosed the use of base-stacking oligomers for DNA sequencing in association with passive DNA sequencing microchips. Moreover, G. Yershov et al., *Proc. Natl. Acad. Sci.* USA, Vol. 93, pp. 4913-4918 (1996), disclosed the application of base-stacking energies in SBH on a passive microchip. In Yershov's example, 10-mer DNA probes were anchored to the surface of the microchip and hybridized to target sequences in conjunction with additional short probes, the combination of which appeared to stabilize binding of the probes. In that format, short segments of nucleic acid sequence could be elucidated for DNA sequencing. Yershov further noted that in their system the destabilizing effect of mismatches was increased using shorter probes (e.g., 5-mers). Use of such short probes in DNA sequencing provided the ability to discern the presence of mismatches along the sequence being probed rather than just a single mismatch at one specified location of the probe/target hybridization complex. Use of longer probes (e.g., 8-mer, 10-mer, and 13-mer oligos) were less functional for such purposes.

An additional example of methodologies that have used base-stacking in the analysis of nucleic acids includes U.S. Pat. No. 5,770,365 by Lane et al., wherein is disclosed a method of capturing nucleic acid targets using a unimolecular capture probe having a single stranded loop and a double stranded region which acts in conjunction with a binding target to stabilize duplex formation by stacking energies.

Despite the knowledge of base-stacking phenomenon, applications as described above have not resulted in commercially acceptable methods or protocols for either DNA sequencing or the detection of SNPs for clinical purposes. We provide herein such a commercially useful method for making such distinctions in numerous genetic and medical applications by combining the use of base-stacking principles and electronically addressable microchip formats.

Kits useful for carrying out the methods of the present invention will, in general, comprise one or more oligonucleotide probes and other reagents for carrying out the methods as described above, such as restriction enzymes, optionally packaged with suitable instructions for carrying out the methods.

The present invention also provides a method of conducting a clinical trial on a plurality of human subjects or patients. Such methods advantageously permit the refinement of the patient population so that advantages of particular treatment regimens (typically administration of pharmaceutically active organic compound active agents) can be more accurately detected, particularly with respect to particular subpopulations of patients. In general, such methods comprise administering a test active agent or therapy to a plurality of subjects (a control or placebo therapy typically being administered to a separate but similarly characterized plurality of subjects) and detecting the presence or absence of at least one mutation or polymorphism as described above in the plurality of subjects. The polymorphisms may be detected before, after, or concurrently with the step of administering the test therapy. The influence of one or more detected polymorphisms or absent polymorphisms on the test therapy can then be determined on any suitable parameter or potential treatment outcome or consequence, including but not limited to: the efficacy of said therapy, lack of side effects of the therapy, etc.

In describing the mutations disclosed herein in the novel proteins described herein, and the nucleotides encoding the same, the naming method is as follows: [nucleic acid replaced] [nucleic acid number in sequence of known sequence] [alternate nucleic acid]. For example, for the 2219 position is guanine and is replaced with an cytosine.

The present invention is explained in greater detail in the following non-limiting examples.

EXAMPLE 1

Identification of Mutations in the Mitofusion 2 Gene Associated with CMT 2A

In all the families identified, different missense mutations in the gene Mitofusin 2 (MFN2) were located. The gene Mitofusin 2 (MFN2) is located 1.65 Mb downstream from the KIF1B locus on chromosome 1p36 (FIG. 1).

Methods

Patients

The CMT2A families DUK662, DUK1706, DUK1241, CMT156 were studied. The Russian family RU45 was ascertained at the Research Center for Medical Genetics, Moscow. The Turkish family CMT166 was identified in collaboration of the University of Istanbul and the University of Antwerp. Controls consisted of unrelated spouses of CMT families and unrelated individuals of Turkish nationality with no clinical signs of peripheral neuropathies. All samples were collected with informed consent. Tissue for RT-PCR was obtained from a human tissue bank at the Department of Neuropathology, University Hospital, Rhineland-Westphalian Technical University. The study was approved by each collaborators institutional review board or equivalent.

Mutation Screening

All PCR primers were designed with the web-based primer3 algorithm. PCR reactions followed standard protocols. PCR products were visualized on 1.5% agarose gels stained with ethidium bromide. The reaction products were purified applying the Qiaquick PCR purification kit (Qiagen, Hilden, Germany). Amplified DNA samples were directly sequenced applying the Big dye Terminator reaction kit (Applied Biosystems, Foster City, USA) on an ABI 3730.

Genes were sequenced for mutation screening in coding exons and flanking intronic sequences in both directions (forward and reverse).

RT-PCR

For transcript analysis at the cDNA level, total RNA was isolated from blood samples using the PAXgene Blood RNA Kit (PreAnalytiX, Hombrechtikon, Switzerland) and RNeasy (Qiagen, Hilden, Germany). The mRNA was reverse transcribed to cDNA with random primers (Reverse Transcription System, Promega, Madison, USA). The KIF1B-β and MFN2 cDNAs were amplified with primer sets, which produced overlapping products.

Genotyping and Linkage Analysis

For genotyping of family RU45 the following microsatellite markers were used to test linkage to the CMT2A locus: D1S2663 (AFMa210xg9), D1S508 (AFMa128ye9), D1S2667 (AFMa224wg9), D1S228(AFM196xb4). A newly designed STR marker at contig AC019262 was amplified by the primers AC019262-F: GGAGTGCATTTCTGCTTGG-TAG (SEQ ID NO: 19) and AC019262-R: AACACTTGGCT-TATACCTTTTCTAG (SEQ ID NO:20). All PCR reactions were performed following standard procedures. Two-point linkage analysis was performed by the programs MLINK and ILINK (LINKAGE package, version 5.1). LOD scores were calculated under the assumption of equal marker allele frequencies, and the disease was assessed as an autosomal dominant trait with a 0.0001 disease allele frequency. The FASTLINK package (version 4.1P) was used for multipoint analysis of data.

Electronic Database Information

Accession numbers and URLs for data presented herein are as follows:

BLAST searches, www.ncbi.nlm.nih.gov/BLAST
Ensembl Genome Browser, www.ensembl.org
Entrez Protein, www.ncbi.nlm.nih.gov/entrez (mitofusin 2, Homo sapiens [accession number AAH17061]; mitofusin 2, *Mus musculus* [accession number AAM88577], mitochondrial assembly regulatory factor, *Drosophila melanogaster* [accession number AAM00196]; mitofusin 2, *Caenorhabditis elegans* [accession number NP_495161]; mitofusin 1, *Homo sapiens* [accession number AAH40557]; mitofusin 1, *Mus musculus* [accession number NP-077162]

ExPASy Molecular Biology Server, www.expasy.ch
GenBank, www.ncbi.nlm.nih.gov/Genbank ([accession number NT_015074], UBE4B [accession number NM_006048], PEX [accession number NM_004565], TARDBP [accession number NM_007375], PMSLC [accession number NM_002685], FRAP1 [accession number NM_004958], KIAA1337 [accession number XM_052561], FBXO2 [accession number NM_012168], FBG3 [accession number NM_033182], FBXO6 [accession number NM_001286], CLCN6 [accession number NM_001286], NPPA [accession numbers NM_006172], NPPB [accession number NM_002521], TNFRSF8 [accession number NM_001243], KIAA0453 [accession number XM_044546], KIF1B [accession number NM_015074], MFN2 [accession number NM_014874], and MFN1 [accession number NM_033540])

Genome Data Base, www.gdb.org
HUGE database, www.kazusa.or.jp/huge (for KIAA1337, KIAA0453)
Inherited Peripheral Neuropathies Mutation Database, molgen-www.uia.ac.be/CMTMutations
MITOPROT, ihg.gsf.de/ihg/mitoprot.html (for prediction of mitochondrial targeting sequences in MFN2)
NCBI Aceview, www.ncbi.nih.gov/IEB/ResearchIAcembly
NCBI dbEST database, www.ncbi.nlm.nih.gov/dbEST/index.html
NCBI dbSNP database, www.ncbi.nlm.nih.gov/entrez/query.fcgi?db=snp
NCBI for protein access,
NCBI RefSeq project, www.ncbi.nih.gov/RefSeq/
Online Mendelian Inheritance in Man (OMIM)
Pfam, pfam.wustl.edu/index.html (for fzo_mitofusin domain [accession number PF04799.2], GTP binding domain [accession number PF00009]), and P-loop motif)
Primer3, www-genome.wi.mit.edu/cgi-bin/primer/primer3.cgi
PSORT, psort.nibb.ac.jp/form.html (for prediction of mitochondrial targeting sequences in MFN2)
SMART, smart.embl-heidelberg.de
SWISS-PROT, www.expasy.org/sprot/
TMHMM, www.cbs.dtu.dk/services/TMHMM/, (for prediction of transmembrane helices in MFN2)
Unigene, www.ncbi.nlm.nih.gov/UniGene
UCSC genome browser, www.genome.ucsc.edu Family Data and Haplotype Analysis The original CMT2A family (DUK662), three previously reported families from Italy (CMT156) and Northern America (DUK1241, DUK1706), and two newly ascertained pedigrees originating from Russia (RU45) and Turkey (CMT166) were studied (FIG. 2, 3). Linkage analysis to the CMT2A locus for all six families provided LOD scores ranging from 2.20 to 5.88 (Table 1).

TABLE 1

Primers and RT-PCR primers for MFN2

| Name | Forward primer | SEQ ID | Reverse primer | SEQ ID |
|---|---|---|---|---|
| Mit-1 | CCATGATGGAGTGGGAGTC | 21 | GCTTGACTGCATCCCAGAC | 22 |
| Mit-2 | GCAAGTCCCCAATACCTCAA | 23 | GAGACTTGCCACCAGAGGTC | 24 |
| Mit-3 | TGATTCTCCCCAAAGCATTC | 25 | TATGAGTTCCCTGGGAGCAG | 26 |
| Mit-4b | ATCTTCTACCAGCCGCCATT | 27 | GGATTGAAAATGGGTCACCA | 28 |
| Mit-4 | CCTTCCAGACTTGGGACTGT | 29 | GCCTGGAACGTTCTGTGAC | 30 |

TABLE 1-continued

Primers and RT-PCR primers for MFN2

| Name | Forward primer | SEQ ID | Reverse primer | SEQ ID |
|---|---|---|---|---|
| Mit-5 | ACTGGCAACATTGCACTGAA | 31 | GTCTCCCATTCACCTCCACA | 32 |
| Mit-6 | CCACTGTGCTGTGATGCAG | 33 | AGGGACCCTGGCCTAGATTA | 34 |
| Mit-7/8 | GTCCCAGGTCTGTTCTCAGC | 35 | CACTAGATCCAGGGGTGCAG | 36 |
| Mit-9 | TCGGAAAGTGGTGGGATTAC | 37 | TCTCAGCATCCCCTTCTCAG | 38 |
| Mit-10 | CTGAGAAGGGGATGCTGAGA | 39 | TCACTGCAGACTGGGAGATG | 40 |
| Mit-11 | TGTGTGCCTCCCCAGGTC | 41 | GGTGGAGCACCCTTGTCTC | 42 |
| Mit-12 | ATTTCTGGGATCCCCTCTTG | 43 | TGAAAGGCTGAGAAGTCCCTA | 44 |
| Mit-13 | GCCATCTGCTAGGATCTCTCC | 45 | TGTCTCTGTGGCTTCTACTGTCA | 46 |
| Mit-14 | CCCAGCAGTGACAGTAGAAGC | 47 | CCAGAACCTGAAGGTATCGAGT | 48 |
| Mit-15 | TGGTAGAGCCCTGTCTCCAA | 49 | TTAGGGAACCCCCGTTTTAG | 50 |
| Mit-16 | GAGGCACTCTGTGTCCCTGT | 51 | CAGTGGACTGTGGAGTGTGG | 52 |
| Mit-17 | GAAACATGAAGGCTCCTTGG | 53 | AGAGAGATGGGGAAGGGAGA | 54 |
| Mit-18 | AGGAGATTGTGGCAAACCAG | 55 | TTTGTGTCCACAGCCAAGAG | 56 |
| Mit-19 | GGTGTGTGTCAAGCGTCCTT | 57 | GATGAAGCACTGAGCCAACA | 58 |
| MitRT ex2-6 | CATGATGCCTACCCTGTGAA | 59 | CCAGACAAAACTTGTCAATCCA | 60 |
| MitRT ex6-12 | TGTGATGTGGCCCAACTCTA | 61 | GACACCTGCCTCTCCACTTC | 62 |
| MitRT ex12-16 | CGGGAGCAGCAGGTTTACT | 63 | CATGGAGGTCCTGGATGTCA | 64 |
| MitRT ex16-19 | TTGATGGGCTACAATGACCA | 65 | TGCTTCATTCTCTTGGCAGT | 18 |

The flanking markers for the CMT2A locus were originally designated by the family DUK62 and were later refined to a 10.0 cM region by recombinants in family CMT156 (ref. 3, 16). The Turkish family CMT166 provided a further reduction of the CMT2A locus to 9.3 cM, defined by the markers D 1 S160 and D IS434 (FIG. 1A). Summarized clinical and electrophysiological data are shown in Table 2.

TABLE 2

Missense mutations (A) and intragenic SNPs (B) detected in MFN2

| | Exon/Intron | CMT2A Family | Nucleotide change | Amino acid change | Ethnic origin | dbSNP number |
|---|---|---|---|---|---|---|
| A | 4 | CMT166 | c.205G > T | Val69Phe | Turkish | |
| | 4 | DUK1706 | c.227T > C | Leu76Pro | Northern American | |
| | 4 | RU45 | c.281G > A | Arg94Gln | Russian | |
| | 8 | CMT156 | c.751C > G | Pro251Ala | Italian | |
| | 9 | DUK1241 | c.839G > A | Arg280His | Northern American | |
| | 19 | DUK662 | c.2219G > C | Trp740Ser | Northern American | |

Description of a Newly Ascertained CMT2A Family

Pedigree RU45 represents a CMT2A family originating from Russia. In all patients of the family the disease is characterized by limb weakness and severe atrophy of the peroneal, distal femoral, and distal hand muscles. Further "stocking and glove" sensory loss, absence of ankle and carpo-radial reflexes, pes cavus, and steppage gait were observed. One affected (marked in grey in FIG. 3) suffered from cerebral palsy; thus his CMT status was not established clearly. Electrophysiological analysis of three affected females demonstrated normal NCV values for the motor median nerve and moderately decreased for the tibial nerve (Table 2). The maximum two-point LOD score of 3.55 was obtained for the marker AC019262, lying near D1 S434.

Mutation Screening in KIF1B

Direct sequencing of the amplified coding exons of KIF1B-β in the families DUK662, DUK1706, DUK1241, RU45, CMT156, and CMT166 revealed no mutations. In addition, direct sequencing of the KIF1B-β cDNA of two affected subjects in families CMT156 and CMT166 revealed no additional sequence variations, deletions or insertions. RT-PCR with primers spanning the entire gene and producing overlapping PCR products did not disclose evidence for additional exons in the vicinity of KIF1B-β in human samples of peripheral nerve tissue. However, this experiment demonstrated a formerly described splice variant of KIF1B-β lacking exon 25. This shorter splice variant of KIF1B-β was present in cDNA retrieved from blood, peripheral nerve, spinal cord, brain, and muscle tissue. The longer isoform was expressed in muscle, spinal cord, and brain.

Several single nucleotide polymorphisms (SNP) distributed over the entire gene were detected in coding exons and flanking intronic sequences in patients and 40 healthy controls. As the KIF1B gene consists of a head and two alternatively spliced tails, α and β, mutations in KIF1B-β were also excluded by sequencing.

Mutation Detection in Mitofusin 2 (MFN2)

The refined chromosomal region of 9.6 cM contains at least 55 known or predicted genes. Candidate genes with known expression in the nervous system were prioritized for mutation analysis. The following genes were screened for mutations in affected individuals from the examined families: UBE4B, PEX, TARDBP, PMSLC, FRAPI, KM4A1337, FBXO2, FBG3, FBXO6, CLCN6, NPPA, NPPB, TNFRSF8, K!AA0453, and MFN2 (FIG. 1). In the gene MFN2, six different missense mutations were identified in the six families. In family DUK662 a c.2219G>C substitution (Trp74OSer) completely co-segregated with the CMT2 phenotype, but was not evident in 250 healthy Caucasian controls. Applying the algorithm by Lupas et al., the exchange from the aromatic tryptophan to the small polar serine was predicted to extend the coiled-coil structure that occurs at the end of the fzo_mitofusin domain (FIG. 1). The mutations in families DUK1241 (c.839G>A, Arg280His) and CMT156 (c.751C>G, Pro251Ala) were found in the GTPase domain of the protein. Both Pro251 and Arg280 amino acids are highly conserved in *Drosophila melanogaster* and *Caenorhabditis elegans*, suggesting functional importance (FIG. 3). In family RU45, an Arg94Gln mutation was caused by a transition of G>A at position 281 (c.281 G>A). This amino acid marks the predicted beginning of the GTPase domain and is conserved in the GTPase domain of MFN 1, a homolog protein of MFN2 (FIG. 3). The mutation in family DUK1706 (Leu76Pro, c.227T>C) also lies at the beginning of the GTPase domain. The Leu76 allele is also conserved in mammals and *D. melanogaster* (FIG. 3). In the Turkish family, CMT 166, an exchange of G>T substitutes Valine for Phenylalanine (c.205G>T, Val69Phe). The Val69 allele is similarly highly conserved in MFN2 (FIG. 3). No mutations were detected in at least 250 healthy control samples.

Expression of MFN2 in Human Neural Tissue

By RT-PCR the presence of MFN2 transcripts was shown in human muscle, sural nerve, spinal cord, and brain. A formerly predicted alternative exon 4*b* (FIG. 1*b*) was verified in all samples. This alternative transcript begins translation at exon 4*b*, leading to a shortening (96 amino acids) at the N-terminal of the protein.

EXAMPLE 2

Additional Mutations Found in CMT 2A Individuals

Using the methods described herein, additional mutations were identified in MFN2 in CMT2 patients. One mutation was a 493 C>G change, resulting in 165His>Asp. This mutation is associated with CMT2 and mild spastic features in the clinical examination, strongly implying the involvement of the central nervous system. The mutation segregated in a large Australian family and was not found in 500 control chromosomes.

Additional mutations are described in Supplementary Tables 1 and 2 below.

Supplementary Table 1 Observed intragenic SNPs in KIF1B-β.

| Exon/Intron | Nucleotide change | Effect on coding sequence | dbSNP number |
|---|---|---|---|
| 4 | c.183 – 2delTT | 5'-splice site | — |
| 4 | c.285C > G | Ala95Ala | — |
| IVS5 | c.429 + 26G > A | — | rs4846209 |
| IVS5 | c.430 – 31A > T | — | — |
| IVS7 | c.720 + 17C > T | — | — |
| IVS13 | c.1296 + 38A > G | — | rs3748576 |
| IVS18 | c.1723 + 125A > G | — | — |
| IVS36 | c.3813 – 53A > T | — | rs4846215 |
| 38 | c.4161A > G | Pro1387Pro | — |
| 46 | c.5163C > A | Thr1721Thr | — |

Supplementary Table 2
MFN2 mutations found in 36 additional CMT2 families that were too small for linkage analysis.

| Family | DUK1265 | DUK2007 | DUK2128 | DUK2158 | DUK2173 | DUK2176 | DUK2451 |
|---|---|---|---|---|---|---|---|
| Ethnic origin | North America | North America | North America | North America | North America | Iran/Iraq | North America |
| Mutation in MFN2 | c.2219G > C; Trp740Ser | c.2219G > C; Trp740Ser | c.839G > A; Arg280His | c.1252C > T; Arg418Stop | c.280C > T; Arg94Trp | c.821G > A; Arg274Gln | c.314C > T; Thr105Met |
| Exon | 19 | 19 | 9 | 12 | 4 | 9 | 5 |
| Age at onset (years) | <10 | 7-47 | 28 | 1 | <10 | 13 | 3-15 |
| Distal weakness and atrophy, UL/LL | +/++ | +/++ | +/+ | ++/+++ | ++/+++ | −/++ | +/+++ |
| Distal sensory loss | + | + | + | + | + | + | + |
| Proximal muscle strenght | normal | normal | normal | normal | normal | normal | normal |
| Other symptoms | — | — | — | visual impairment | migraine | — | ataxia, scoliosis |
| Achilles tendon reflex | absent | absent | absent | absent | absent | absent | absent |
| Motor NCV, Median nerve (m/s) | not obtained | 40-49 | 49 | 52 | 47 | 58 | 47-52 |

+, mild; ++, moderate; +++, severe; UL, upper limbs; LL, lower limbs; NCV, nerve conduction velocity The Arg418X change in MFN2, described above in Supplementary Table 2, caused a premature termination of translation in on of the CMT2 patients. The clinical phenotype of this patient included early age at onset, vocal cord paresis with hoarse voice, and visual impairment. The visual impairment is due to pathologic changes of the retina that resembles phenotypes known from mitochondrial disease and also from optic atrophy. Therefore, a portion of patients diagnosed as Leber hereditary optic atrophy without mutations in the mitochondrial genome might well have mutations in MFN2.

The foregoing is illustrative of the present invention, and is not to be construed as limiting thereof. The invention is defined by the following claims, with equivalents of the claims to be included therein.

What is claimed is:

1. A method of screening a human subject for risk of Charcot-Marie-Tooth Disease Type 2A comprising:
   assessing a biological sample collected from said subject for the presence of mutations in the mitofusin 2 gene, wherein the mutations comprise a C to T change at position 280 or a G to A change at position 281 in the coding sequence of the mitofusin 2 gene, or a mutation in the coding sequence of the mitofusin 2 gene that results in alteration of the arginine at position 94 in an amino acid sequence of mitofusin 2; and
   determining whether the subject is at an increased risk of Charcot-Marie-Tooth Disease Type 2A,
   wherein the presence of any one of said mutations in the mitofusin 2 gene is indicative of an increased risk.

2. The method according to claim 1, wherein said biological sample comprises a chromosomal nucleic acid.

3. The method according to claim 2, wherein the chromosomal nucleic acid is Chromosome 1 or a fragment thereof.

4. The method according to claim 1, wherein a mutation results in a change in the amino acid sequence selected from the group consisting of Arg94Gln, and Arg94Trp.

5. The method of claim 1, wherein said assessing step further comprises detecting whether said subject is homozygous for said mutation.

6. The method of claim 1, wherein said assessing step further comprises detecting whether said subject is heterozygous for said mutation.

7. A method for detecting the presence of a mutation associated with Charcot-Marie-Tooth Disease Type 2A in a sample of human patient nucleic acid, comprising:
   amplifying a mitofusin 2 gene sequence in the patient nucleic acid to produce an amplification product;
   assessing the amplification product for the presence of mutations associated with Charcot-Marie-Tooth Disease Type 2A, wherein said mutations comprise a C to T change at position 280 or a G to A change at position 281 in the coding sequence of the mitofusin 2 gene, or a mutation in the coding sequence of the mitofusin 2 gene that results in an alteration of the arginine at position 94 in an amino acid sequence of mitofusin 2, and
   identifying the presence of any one of said Charcot-Marie-Tooth Disease Type 2A genetic mutations within the amplification product.

8. The method according to claim 7, wherein the Charcot-Marie-Tooth Disease Type 2A mutation is identified by sequencing the amplification product.

9. The method according to claim 8, further comprising digesting the amplification product with a restriction enzyme and identifying the Charcot-Marie-Tooth Disease Type 2A mutation by sequencing a restriction fragment.

10. The method according to claim 7, wherein said mutation results in a change in the amino acid sequence selected from the group consisting of Arg94Gln, and Arg94Trp.

11. A method of diagnosing Charcot-Marie-Tooth Disease or a genetic predisposition for developing Charcot-Marie-Tooth Disease in a human subject, comprising:
   providing a biological sample from the subject wherein said sample comprises a mitofusin 2 gene;
   assessing the sample for mutations in the mitofusin 2 gene, wherein the mutations comprise positions a C to T change at position 280 or a G to A change at position 281 in the coding sequence of the mitofusin 2 gene, or a mutation in the coding sequence of the mitofusin 2 gene that results in an alteration of the arginine at position 94 in an amino acid sequence of mitofusin 2; and
   determining that the subject has at least one of said mutations in at least one genomic copy of the mitofusin 2 gene, wherein the presence of at least one of said mutations in the mitofusin 2 gene is diagnostic for Charcot-Marie-Tooth Disease or a genetic predisposition for developing Charcot-Marie-Tooth Disease in the subject.

12. The method according to claim 11, wherein said mutation results in a change in the amino acid sequence selected from the group consisting of Arg94Gln, and Arg94Trp.

13. The method according to claim 11, wherein said determining step further comprises detecting whether said subject is heterozygous for said mutation.

14. The method according to claim 11, wherein said determining step further comprises detecting whether said subject is homozygous for said mutation.

15. The method according to claim 1, further comprising assessing the biological sample for one or more additional mutations in the coding sequence of the mitofusin 2 gene selected from the group consisting of: G2219C, C1252T, G839A, G821A, C751G, C493G, C314T, T227C and G205T, wherein the presence of any one of said mutations is indicative of an increased risk.

16. The method according to claim 1, further comprising assessing the biological sample for one or more additional mutations in the coding sequence of the mitofusin 2 gene that result in an alteration in the amino acid sequence of mitofusin 2, selected from the group consisting of: Trp740Ser; Arg418Stop, Arg280His, Arg274Gln, Pro251Ala, His165Asp, Thr105Met, Leu76Pro and Val69Phe, wherein the presence of any one of said mutations is indicative of an increased risk.

17. The method according to claim 7, further comprising assessing the amplification product for one or more additional mutations in the coding sequence of the mitofusin 2 gene selected from the group consisting of: : G2219C, C 1252T, G839A, G821A, C751G, C493G, C314T, T227C and G205T.

18. The method according to claim 7, further comprising assessing the amplification product for one or more additional mutations in the coding sequence of the mitofusin 2 gene that result in an alteration in the amino acid sequence of mitofusin 2, selected from the group consisting of: Trp740Ser; Arg418Stop, Arg280His, Arg274Gln, Pro251Ala, His165Asp, Thr105Met, Leu76Pro and Val69Phe.

19. The method according to claim 11, further comprising assessing the biological sample for one or more additional mutations in the coding sequence of the mitofusin 2 gene selected from the group consisting of: G2219C, C1252T, G839A, G821A, C751G, C493G, C314T, T227C and G205T, wherein the presence of any one of said mutations is diagnostic for Charcot-Marie-Tooth Disease or a genetic predisposition for developing Charcot-Marie-Tooth Disease.

20. The method according to claim 11, further comprising assessing the biological sample for one or more additional mutations in the coding sequence of the mitofusin 2 gene that result in an alteration in the amino acid sequence of mitofusin 2, selected from the group consisting of: Trp740Ser; Arg418Stop, Arg280His, Arg274Gln, Pro251Ala, His165Asp, Thr105Met, Leu76Pro and Val69Phe, wherein the presence of any one of said mutations is diagnostic for Charcot-Marie-Tooth Disease or a genetic predisposition for developing Charcot-Marie-Tooth disease.

* * * * *